United States Patent [19]

Vail

[11] Patent Number: 5,023,182

[45] Date of Patent: Jun. 11, 1991

[54] NOVEL VIRUS COMPOSITION TO PROTECT AGRICULTURAL COMMODITIES FROM INSECTS

[75] Inventor: Patrick V. Vail, Fresno, Calif.

[73] Assignee: The United States of America as represented by the Secretary of Agriculture, Washington, D.C.

[21] Appl. No.: 212,641

[22] Filed: Jun. 28, 1988

[51] Int. Cl.$^5$ .................. C12N 7/00; C12N 7/02; A01N 25/00; A01N 25/08
[52] U.S. Cl. .................. 435/235.1; 435/239; 424/93; 424/405; 424/409; 424/410
[58] Field of Search .................. 435/235, 239, 235.1; 424/93, 405, 409, 410

[56] References Cited

U.S. PATENT DOCUMENTS

| | | | |
|---|---|---|---|
| 4,217,367 | 8/1980 | Hawley | 426/2 |
| 4,668,511 | 5/1987 | Aspirot et al. | 424/93 |
| 4,870,023 | 9/1989 | Fraser et al. | 435/235 |

OTHER PUBLICATIONS

Langridge et al., *Journal of General Virology*, vol. 54, pp. 443–448 (1981).
Goodwin et al., *In Vitro*, vol. 14(6), pp. 485–494 (1978).
Gaspargan et al., *Chemical Abstracts*, vol. 102:3515g (1985).
D. K. Hunter and D. F. Hoffman, "A Granulosis Virus of the Almond Moth, *Cadra cautella*", *Journal of Invertebrate Pathology* 16: 400–407 (1970).
D. K. Hunter, D. F. Hoffman, and S. J. Collier, "Pathogenicity of a Nuclear Polyhedrosis Virus of the Almond Moth, *Cadra cautella*", *Journal of Invertebrate Pathology* 21: 282–286 (1973).
C. M. Ignoffo, "Development of a Viral Insecticide: Concept to Commercialization", *Experimental Parasitology* 33: 392–393 (1973).
Carlo M. Ignoffo, "The First Viral Pesticide: Past, Present, and Future", Ch. 9, *Development in Industrial Microbiology*, p. 108 (1979).
Frances Greer, Carlo M. Ignoffo, and Ralph F. Anderson, "The First Viral Pesticide: A Case History," *Chem Tech.*, pp. 342–347 (1971).
C. M. Ignoffo, "Insect Viruses", Chapter 36, In; *Insect Colonization and Mass Production*, Ed. C. N. Smith, Academic Press, New York, pp. 501–530 (1966).
*Baculoviruses for Insect Pest Control: Safety Considerations*, Eds. M. Summers, R. Engler, L. A. Falcon, and P. V. Vail, American Society for Microbiology Washington, D.C. (1975), p. 7.
D. K. Cowan, P. V. Vail, M. L. Kok-Yokomi, and F. E. Schreiber, "Formulation of a Granulosis Virus of *Plodia interpunctella* (H',uml/u/ bner) (Lipidoptera: Pyralidae): Efficacy, Persistence, and Influence on Oviposition and Larval Survival", *Journal of Economic Entomology* 79: 1085–1090 (1986).
G. L. Finney and D. Brinkman, "Rearing the Navel Orangeworm in the Laboratory", *Journal of Economic Entomology* 60: 1109–1111 (1967).
D. K. Hunter, S. J. Collier, D. F. Hoffmann, "Effectiveness of a Granulosis Virus of the Indian Meal Moth as a Protectant for Stored Inshell Nuts: Preliminary Observations," *Journal of Invertebrate Pathology* 22: 481 (1973).
D. K. Hunter, S. S. Collier, and D. F. Hoffman, "Granulosis Virus of the Indian Meal Moth as a Protectant for Stored Inshell Almonds", *Journal of Economic Entomology* 70: 493–494 (1977).
D. K. Hunter, S. S. Collier, and D. F. Hoffman, "The Effect of a Granulosis Virus on *Plodia interpunctella* (Hübner) (Leipoptera: Pyralidae) Infestations Occuring in Stored Raisins", *Journal of Stored Products Research* 15: 65–69.
W. H. McGaughey, "A Granulosis Virus for Indian Meal Moth Control in Stroed Wheat and Corn", *Journal of Economic Entomology* 68: 346–348 (1975).

*Primary Examiner*—Esther L. Kepplinger
*Assistant Examiner*—Janelle Graeter
*Attorney, Agent, or Firm*—M. Howard Silverstein; John D. Fado; Margaret A. Connor

[57] ABSTRACT

A potent, stable virus composition useful for protecting agricultural commodities from insects and a simple, efficient, economical and labor-saving method to produce and formulate large quantities of the virus composition are described. The method is particularly useful to prepare nuclear polyhedrosis virus or granulosis virus compositions for control of postharvest pests such as the Indianmeal moth.

7 Claims, No Drawings

NOVEL VIRUS COMPOSITION TO PROTECT AGRICULTURAL COMMODITIES FROM INSECTS

BACKGROUND OF THE INVENTION

1. Field of the Invention

The invention relates to a novel virus composition useful for protecting agricultural commodities from insect pests and preparation thereof.

2. Description of the Art

Baculoviruses, in particular nuclear polyhedrosis viruses (NPVs) and granulosis viruses (GVs), have many characteristics which make them particularly suitable for control of insects. NPVs and GVs are specific in their pathogenicity to the class Insecta and many are highly virulent to their hosts (*Baculoviruses for Insect Pest Control: Safety Considerations*, Ed. M. Summers et al., American Society for Microbiology, Washington, D.C., p. 7, 1975). Such viruses can be used to control insects which infest agricultural commodities such as the Indianmeal moth, the raisin moth, the almond moth, the tobacco moth and the like. A major problem in the use of baculoviruses to control insects is the lack of methods to readily produce large quantities of virus at low cost.

The problem of protecting agricultural commodities from insects is illustrated with reference to the Indianmeal moth, *Plodia interpunctella* (Hübner) (Lepidoptera: Pyralidae), hereinafter IMM. This insect is recognized as a major insect pest that infests grains, dried fruits and nuts, and other stored commodities worldwide. Presently, there is no protection for commodities such as dried fruits and nuts from IMM invasion or damage after the commodities have left the processing plant, and it has been estimated that over 90% of the losses caused by insects to dried fruits and nuts after processing are due to IMM. One problem in controlling IMM is that it has shown resistence to certain chemical insecticides, thus other possible control agents are being investigated.

Granulosis virus (GV) isolated from IMM is a highly virulent insect specific virus; it has been shown to be an effective protectant against IMM for stored dried nuts (Hunter et al., *Journal of Invertebrate Pathology* 22: 481 (1973) and *Journal of Economic Entomology* 70: 493-494 (1977)), raisins (Hunter et al., *Journal of Stored Products Research* 15: 65-69 (1979)), and wheat and corn (McGaughey, *Journal of Economic Entomology* 68: 346-348 (1975)). Because GV is unique to insects and does not infect man, it offers potential for use as a protectant against IMM on food commodities.

Until 1979, formulations of the IMM granulosis virus (IMMGV) were produced by rearing IMM larvae infected with GV on a diet and removing the infected larvae by hand from the diet. After removal, a given number of infected larvae were homogenized in distilled water to free the virus from the insect bodies, and the virus was used immediately. Alternatively, hand-collected larvae were freeze-dried and then homogenized and suspended in water just prior to use. The primary deficiency of this method was that hand-removal of the larvae from the rearing diet was tedious and time consuming and made this method of control of IMM on commodities economically unfeasible. Further, these wet formulations had the problems that loss of activity of the labile nonoccluded infectious components occurred, and the preparation process had to be repeated whenever inoculum was required.

Cowan et al., *Journal of Economic Entomology* 79: 1085-1090 (1986) described a freeze-dried formulation of IMMGV. This formulation was prepared by rearing GV-infected IMM larvae on a diet, and homogenizing the larvae in the diet to obtain a composition containing GV-infected larvae plus the diet components. The composition was freeze-dried, milled, and formulated with a carrier, and the formulation tested for control of IMM on almonds and raisins. The diet components used to rear the IMM larvae consisted of wheat bran, honey, water, glycerol, a vitamin mixture, and fungicides/fungistats. The problems associated with this composition (GV-infected larvae plus diet components) are that the presence of honey and glycerol caused the formulations after freeze-drying to be sticky and difficult to mill as well as hygroscopic. Attempts to minimize these problems included washing the formulation several times prior to homogenizing and freeze-drying. However, even with several washings, not all the glycerol and honey was washed out. In addition to adding additional labor with attendant increased costs, the washing procedure resulted in significant losses in potency of the formulation.

SUMMARY OF THE INVENTION

The present invention provides a simple, efficient, and labor-saving method to produce and formulate large quantites of virus for use as an agricultural commodity protectant at less than one tenth the cost of the wet formulations and at significantly less than the cost of the Cowan et al. formulation, while eliminating the problems associated with the prior art methods.

In the method of the invention, host larvae are reared on a diet devoid of honey and glycerol, components which provide sources of readily-utilizable sugars, vitamins, and trace minerals. Heretofore it was thought that honey and glycerol were nutritional components essential for larvae growth and development. Surprisingly, however, removal of these "critical" components from the diet did not deter larval growth or consequent virus production, and further, resulted in a 20-30 fold increase in activity over the Cowan et al. formulations, while eliminating the washing steps of Cowan et al.

With regard to the earlier formulations wherein the infected larvae were hand-removed from the diet, the instant method provides a labor-saving method to produce and formulate large quantities of virus at less than one tenth previous costs. The dry formulation of the invention is also much easier to assay and store, and eliminates the need of making wet formulations for laboratory or commercial use.

In accordance with this discovery, it is an object of the invention to provide a method for preparing a virus composition useful to protect agricultural commodities against insects.

A further object of the invention is to provide virus compositions devoid of honey and glycerol which are useful as commercial insecticides.

Another object of the invention is the provision of a simple, cost-saving, efficient method to obtain large quantities of virus for use to control insects in raw agricultural commodities, in stored commodities after harvesting and processing, in packaged commodities, and in warehouses or processing plants. The invention provides a way to protect commodities from insects through marketing channels to consumption.

Other objects and advantages of the invention will become readily apparent from the ensuing description.

DETAILED DESCRIPTION OF THE INVENTION

The invention comprises preparation of a virus composition for use in protecting agricultural commodities from insects while eliminating honey and glycerol from the larvae-virus production diet and eliminating the hand-removal of larvae.

Preparation of the Virus composition of the Invention.

Step 1. Preparation of the Diet.

A diet is prepared which contains a substrate which functions simultaneously as a nutritional component for the host larvae (larvae which are to serve as hosts for production of the virus), a substrate to absorb excess moisture in the diet, a bulking agent, and a carrier for other components. Examples of such a substrate are wheat bran and rice bran. The preferred substrate is wheat bran. Other components in the diet are water added in an amount sufficient to disperse the diet components on the substrate; yeast, preferably Brewers yeast, in an amount sufficient to provide vitamin complexes necessary for growth; and vitamins. Optional ingredients include fungicides or fungistats. It is a critical feature of the invention that honey and glycerol be omitted from the diet.

Step 2. Infestation and First Incubation.

The diet described in step 1 is infested with sufficient insect eggs or larvae to adequately utilize the diet without adversely affecting virus production, and incubated for a time and at a temperature to develope the larvae to the middle stages of larval development, e.g., until they are about half-grown. In the case of the IMM, for example, suitable development generally is obtained in about 10 days when the temperature is 27±1° C.

Step 3. Inoculation of the Infested Diet and Second Incubation.

An inoculum of virus is prepared by homogenizing virus-infected larvae in water by any standard method, for example, as described by Cowan et al., supra. The diet plus infested larvae from step 2 is inoculated with the virus inoculum and incubated for a second incubation for a time and at a temperature sufficient to cause the larvae to become infected with the virus. In the case of production of IMMGV, for example, at least 90% of the larvae will become highly infected, that is will have patent infection or be moribund, in about 10 days at 27±1° C.

Step 4. Homogenization.

Next, sufficient water is added to homogenize the diet plus virus-infected larvae obtained in step 3, and the mixture is homogenized to have the consistency of a slurry. Homogenization must be carried out at temperatures which do not adversely affect the activity of the virus. Temperatures below about 27° C. are preferred.

Step 5. Recovery of the Homogenate.

Next, the homogenate is dried by a method which removes water without adversely affecting virus activity, for example, freeze-drying, and the dried material is milled to a fine powder at temperatures which do not adversely affect the activity of the virus in the composition.

The virus composition can be used immediately or it can be stored refrigerated or frozen for future use.

Application of the Virus Composition.

The virus composition prepared as described in steps 1-5 is applied by any method known to those in the art for microbial agents used for insect control. For example, it may be formulated with water to provide an aqueous suspension for spraying on commodities. To prepare the suspension, the virus composition is mixed with sufficient water to provide coverage of the commodity with the virus composition without raising the water content of the commodity such that mold or other adverse problems occur. Generally about 0.5-1% (w/w, water/commodity) is suitable. Alternately, the virus composition is added to a carrier, for example, milled wheat bran, to obtain a dust formulation for dusting on the commodity to be protected. In all cases, the amount of virus in the application formulation must be a pesticidally effective amount, that is, an amount which will result in a significant mortality rate of a treated group as compared to an untreated group. The actual effective amount may vary with the species of pest, type of virus, and other related factors. For most applications, it is preferred to achieve an $LC_{95}$ (concentration that kills 95% or more of exposed insects) dose/gram of commodity based on quality control bioassays.

It is preferred that the virus composition comprise baculovirus, particularly nuclear polyhedrosis virus or granulosis virus, as these viruses are restricted in their pathogenicity to the class Insecta, are often genus or species specific, and are often highly virulent to their hosts. Further, they can be used in insect control programs without harm to beneficial arthropod species.

Uses.

The virus composition of the invention is useful as a protectant for commodities after harvest and particularly as a protectant for commodities after processing. However, it can be used on raw agricultural commodities as well. The composition may also be used in warehouses, processing plants, and other areas in sanitation programs to reduce risk of infestation of the commodities. It is also useful for topically treating packaged commodities to kill larvae prior to entering the packages.

Another use of the formulation is in combination with an insect attractant to attract and contaminate insect adults and thus disseminate the virus into the environment of the target insect.

The virus composition finds particular use in controlling postharvest pests such as the IMM, the raisin moth, the tobacco moth, the almond moth and the like. For example, the IMMGV composition is useful as a microbial control agent for IMM infesting dried fruits and nuts and grains; it provides excellent control of IMM at a cost similar to that of the presently used pesticides.

It was unexpected that a diet devoid of honey and glycerol would be useful for larvae growth, as it was thought that these components provided nutrients essential for growth and development of the larvae. Surprisingly, however, not only did the larvae grow on the diet, removal of these components resulted in a 20-30 fold increase in activity of the resulting virus composition as compared to the Cowan et al. preparation. Further, the need for washing these components out of the diet was eliminated.

EXAMPLES

The following examples are intended only to further illustrate the invention and are not intended to limit the scope of the invention which is defined by the claims.

EXAMPLE 1

IMM eggs and neonate larvae were obtained from stock colonies reared at the U.S. Department of Agriculture Agricultural Research Service Horticultural Crops Research Laboratory, Fresno, Calif. Eggs were surface-sterilized in 10% formalin for 20 minutes and washed with sterile, distilled water for 30 minutes.

A diet was prepared which contained 3 gallons of autoclaved wheat bran; 400 ml deionized water; 100 gram Brewers yeast, and 0.1 gm Vanderzants vitamin mixture in 10 ml water. Sorbic acid and methyl-p-hydroxybenzoate (4,000 ppm each) were mixed into the diet as fungistats. After preparation, 150 grams of the diet was placed in 0.95 liter wide-mouth canning type jars, the metal lids of which were replaced by fine-mesh brass screen discs and filter paper circles (9 cm diam). The jars were infested with 100 mg of IMM eggs, closed, and incubated at 26.7±1° C. for 10 days. Next, the jars were inoculated with an aqueous spray containing approximately 93 mg of homogenized, GV-diseased IMM larvae in 25 ml of sterile distilled water. The inoculum was lightly stirred into the diet-larvae mixture. The diseased IMM larvae-diet mixture was then incubated for an additional 10 days at 26.7±1° C.

Next, 200 ml of cold, sterile, distilled water was added to the larvae-diet mixture, and the mixture was homogenized into a fine slurry and freeze-dried. Care was taken to maintain the temperature of the slurry below about 27° C. The preparation was then milled into a fine powder, with care taken to avoid inactivation temperatures. After milling, the preparation was passed through a fine sieve to eliminate any coarse particles that may have remained and also to prevent clogging of nozzles if an aqueous spray is used.

Bioassay Procedure. To determine viral activity, the GV composition was diluted in sterile distilled water so that the addition of 4 ml of the dilutions per 20 g of maintenance diet (Cowan et al., supra) provided concentrations between 1.0 mg/g and 0.001 microgram/g depending on the potency of the formulation. After thorough mixing, each of two cups (236 ml each) per concentration were infested with 50 newly hatched IMM larvae and were covered with a plastic lid and incubated to adult emergence. Mortality was based on the number of moths emerging from each concentration. Controls were prepared identical to the samples except that GV composition was not added.

The results are shown in Table 1. As can be seen from the data, the GV composition showed $LC_{50}$ values in the range of 0.22 (0.19–0.26) microgram/gm of larval diet for formulations resulting from the above preparation. This preparation maintained its activity after storage for 22 months at −20° C. (Table 1).

For comparison purposes, the above preparation was carried out except that honey and glycerol were included in the diet for virus production, and subsequently the honey and glycerol were washed out of the formulation (Cowan et al., supra). Bioassays of the resulting preparation showed $LC_{50}$ values in the range of 5.6 (2.2–10.7) micrograms/gm of larval diet. This amounts to approximately a 25-fold difference in potency between the formulation of the invention and the formulation of Cowan et al.

TABLE 1

| GV Composition | | Potency (micrograms GV per gram diet) (95% CL) | | |
|---|---|---|---|---|
| Sample | Bioassay date(s) | $LC_{50}$ | $LC_{95}$ | $LC_{99}$ |
| F-12-12-20 | 3/86–10/86 | 0.22 (0.19–0.26) | 3.64 (2.72–4.87) | 11.61 (7.89–17.10) |
| F-12-12-20[1] | 1/88 | 0.40 (0.23–0.62) | 3.87 (2.09–11.63) | 9.93 (4.41–46.10) |

[1]Stored for 22 months at −20° C.

Use as Commodity Protectant. The GV composition prepared as described above was tested for control of IMM on raisins as follows. The GV composition was added to water to provide an aqueous spray that would treat the raisins at 10 mg or 100 mg GV composition per kg of raisins. The spray was applied to the raisins at a rate of 0.75% (w/w, water/raisins). Next, the raisins were artificially infested with IMM eggs and incubated until adult emergence was complete. Percent survival of IMM adults and percent visually damaged raisins were measured. The results are shown in Table 2. As can be seen from the data, damage to the raisins and survival of IMM adults were significantly reduced by treatment with the GV composition.

TABLE 2

| GV dose[1] (mg/kg) | % raisins damaged | % survival to adult |
|---|---|---|
| 0 (control) | 86 | 2.3 |
| 10 | 30 | 1.1 |
| 100 | 3 | 0.1 |

[1]Composition F-12-12-20.

It is understood that the foregoing detailed description is given merely by way of illustration and that modification and variations may be made therein without departing from the spirit and scope of the invention.

What is claimed is:

1. A method for preparing a dry virus composition useful to control a postharvest insect which is susceptible to infection by a baculovirus selected from the group consisting of nuclear polyhedrosis virus (NPV) and granulosis virus (GV), which comprises:

(a) preparing a diet which consists essentially of (i) a substrate which serves as a nutritional component for larvae of a postharvest insect which is susceptible to infection by a baculovirus selected from the group consisting of NPV and GV, as a bulking agent, and as a carrier for other diet components; (ii) yeast in an amount sufficient to provide vitamins for larval growth, (iii) vitamins, and (iv) water in an amount sufficient to disperse diet components on said substrate, wherein said diet is devoid of glycerol and honey;

(b) infesting said diet with said postharvest insect eggs or larvae and incubating said infested diet to develop said eggs or larvae to the middle stages of larval development;

(c) inoculating said infested, incubated diet of step (b) with virus inoculum comprising said baculovirus and incubating for a sufficient time for said larvae to become infected with said baculovirus;

(d) homogenizing said inoculated, incubated mixture of step (c) in water; and (e) drying said homogenate at temperatures which do not adversely affect the activity of said baculovirus in the composition to obtain a virus composition useful to control said postharvest insect.

2. A method of controlling a postharvest insect which is susceptible to infection by a baculovirus selected from the group consisting of NPV and GV, which comprises applying said virus composition prepared in accordance with the method of claim 1 to an agricultural commodity in a pesticidally effective amount.

3. The method of claim 1 wherein said substrate in step (a) is wheat bran or rice bran.

4. A virus composition prepared by the method of claim 1.

5. A stable, potent dry virus composition which comprises NPV or GV virus-infected larvae of a postharvest insect which is susceptible to infection by a baculovirus selected from the group consisting of NPV and GV and a larval growth diet consisting essentially of (i) a substrate which serves as a nutritional component for said insect larvae, as a bulking agent, and as a carrier for other diet components; (ii) yeast in an amount sufficient to provide vitamins for larvae growth, and (iii) vitamins, wherein said diet is devoid of glycerol and honey.

6. The composition of claim 5 wherein said virus is granulosis virus and said insect is the Indianmeal moth.

7. A method for protecting an agricultural commodity from a postharvest insect which is susceptible to infection by a baculovirus selected from the group consisting of NPV and GV, which comprises applying to the agricultural commodity a pesticidally effective amount of the virus composition of claim 5.

* * * * *